(12) United States Patent
Avery et al.

(10) Patent No.: US 9,381,304 B2
(45) Date of Patent: Jul. 5, 2016

(54) CARTRIDGE HOLDER AND ALIGNMENT INTERFACE

(75) Inventors: Richard James Vincent Avery, Gloucestershire (GB); Aled Meredydd James, West Midlands (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 352 days.

(21) Appl. No.: 13/641,801

(22) PCT Filed: Apr. 21, 2011

(86) PCT No.: PCT/EP2011/056475
§ 371 (c)(1),
(2), (4) Date: Dec. 21, 2012

(87) PCT Pub. No.: WO2011/131778
PCT Pub. Date: Oct. 27, 2011

(65) Prior Publication Data
US 2013/0096509 A1      Apr. 18, 2013

Related U.S. Application Data

(60) Provisional application No. 61/327,288, filed on Apr. 23, 2010.

(30) Foreign Application Priority Data

Jul. 29, 2010   (EP) .................................... 10171165

(51) Int. Cl.
  *A61M 5/31*   (2006.01)
  *A61M 5/24*   (2006.01)
  (Continued)

(52) U.S. Cl.
  CPC .............. *A61M 5/3129* (2013.01); *A61M 5/24* (2013.01); *A61M 5/347* (2013.01); *A61M 5/3158* (2013.01);
  (Continued)

(58) Field of Classification Search
  CPC ..... A61M 5/3129; A61M 5/347; A61M 5/24; A61M 5/31593; A61M 5/3158; A61M 5/31551; A61M 2005/2407; A61M 5/31561; A61M 2205/6036
  USPC .......................................... 604/189, 200, 232
  See application file for complete search history.

(56) References Cited

U.S. PATENT DOCUMENTS 5,693,027 A  * 12/1997  Hansen .................. A61M 5/24
                                                                604/200
6,585,698 B1 * 7/2003  Packman ................ A61M 5/24
                                                                604/207

(Continued)

FOREIGN PATENT DOCUMENTS

WO    2008/000827    1/2008
WO    2008/059063    5/2008

OTHER PUBLICATIONS

International Preliminary Report on Patentability for Int. App. No. PCT/EP2011/056475, mailed Nov. 1, 2012.
International Search Report for Int. App. No. PCT/EP2011/056475, completed Jul. 15, 2011.

*Primary Examiner* — Theodore Stigell
*Assistant Examiner* — Amber Stiles
(74) *Attorney, Agent, or Firm* — McDonnell Boehnen Hulbert & Berghoff LLP

(57) ABSTRACT

A system for a drug delivery device comprising a reservoir holder configured to hold a reservoir, and an alignment interface comprising a main body configured to be coupled to the reservoir. A first alignment feature is provided on the main body. The first alignment feature cooperates with a corresponding alignment feature provided by the reservoir holder such that when the reservoir is inserted into the holder, the first alignment feature cooperates with the corresponding alignment feature provided by the holder so as to rotate the alignment interface and thereby align the alignment interface within the holder. Thus, the reservoir may be aligned within the reservoir holder. The first alignment feature may comprise at least one protrusion provided on the main body of the interface. The system further comprises one or more coding features.

17 Claims, 7 Drawing Sheets

(51) Int. Cl.
  *A61M 5/34* (2006.01)
  *A61M 5/315* (2006.01)
(52) U.S. Cl.
  CPC ........ *A61M 5/31551* (2013.01); *A61M 5/31561* (2013.01); *A61M 5/31593* (2013.01); *A61M 2005/2407* (2013.01); *A61M 2205/6036* (2013.01)

(56) References Cited

U.S. PATENT DOCUMENTS

2004/0243065 A1    12/2004   McConnell et al.
2005/0065476 A1     3/2005   Jensen et al.
2006/0079149 A1*    4/2006   Proch .................. A63H 17/008
                                                         446/431

* cited by examiner

CARTRIDGE HOLDER AND ALIGNMENT INTERFACE

CROSS REFERENCE TO RELATED APPLICATIONS

The present application is a U.S. National Phase Application pursuant to 35 U.S.C. §371 of International Application No. PCT/EP2011/056475 filed Apr. 21, 2011, which claims priority to U.S. Provisional Patent Application No. 61/327,288 filed Apr. 23, 2010 and European Patent Application No. 10171165.3 filed Jul. 29, 2010. The entire disclosure contents of these applications are herewith incorporated by reference into the present application.

FIELD OF INVENTION

Embodiments of the present disclosure refer to reservoirs, particularly reservoirs containing a medicament. More particularly, the present disclosure is generally directed to an alignment interface for use with a reservoir and a reservoir holder so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen-type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin, human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

For example, with respect to insulin, a patient suffering from diabetes may require a certain amount of insulin to either be injected via a pen-type injection syringe or infused via a pump. With respect to certain known reusable pen-type drug delivery devices, a patient may load a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user may dispose of the empty cartridges properly. Where the drug delivery device comprises a disposable device, once the cartridge is empty, the user is recommended to dispose of the entire device.

US2004243065 describes apparatuses and methods for a connection interface between a reservoir or syringe, infusion set tubing, and an infusion pump. A base is provided which is adapted to receive a reservoir and engage a cap. When the reservoir, the base and the cap are connected to form an integrated unit, this unit is then capable of being inserted and secured in the infusion pump housing.

Such known administration systems requiring the removal and reloading of empty cartridges have certain limitations. For example, in certain generally known systems, a user simply may load a new cartridge into the delivery system without the drug delivery device or without the cartridge having any mechanism of preventing cross use of an incorrect cartridge. That is, the drug delivery device does not have a mechanism for determining whether the medicament contained in the cartridge is indeed the correct type of medicament to be administered by the patient. Alternatively, certain known drug delivery devices do not present a mechanism for determining whether the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and must comply with certain recognized local and international standards. Consequently, such cartridges are typically supplied in standard sized cartridges (e.g. 3 ml cartridges). Therefore, there may be a variety of cartridges supplied by a number of different suppliers and containing different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that may only accept or work with the dedication or coded features provided on or with the cartridge so as to prevent unwanted cartridge cross use. Similarly, there is also a general need for a dedicated cartridge that may allow the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e. making it more difficult for counterfeiters to provide unregulated counterfeit medicament carrying products.

These and other advantages and features will become evident from the following more detailed description of the disclosure.

One problem to be solved by the present disclosure is to provide a system for a drug delivery device and a drug delivery system where the safety of the user is increased.

SUMMARY

According to an exemplary arrangement, an alignment interface configured to align a reservoir within a reservoir holder is provided. The alignment interface may comprise a main body. The main body may be configured to be permanently or releasably coupled to the reservoir. The alignment interface may comprise a first alignment feature. The first alignment feature may be provided on the main body. When the alignment interface is inserted into the holder, the first alignment feature cooperates, in particular mechanically cooperates, with a corresponding alignment feature. The corresponding alignment feature may be provided by the reservoir holder. The first alignment feature and the corresponding alignment feature may cooperate so as to rotate the alignment interface and thereby align the alignment interface within the holder. By aligning the alignment interface, a reservoir that is coupled to the main body of the alignment interface may be aligned to the reservoir holder. The first alignment feature may comprise at least one protrusion and/or at least one groove provided on the main body of the alignment interface.

According to an embodiment, a system for a drug delivery device is provided. The system may comprise a reservoir holder, e.g. a cartridge holder configured to hold a reservoir. The system may further comprise a reservoir or cartridge. The reservoir may hold at least one dose, preferably a plurality of doses of a medicament. The system may further comprise an alignment interface. The alignment interface may be configured to align the reservoir within the reservoir holder. The alignment interface may comprise a main body. The main body may be configured to be permanently or releasably coupled to the reservoir. The alignment interface may comprise a first alignment feature. The first alignment feature may be provided on said main body. The reservoir holder may comprise a corresponding alignment feature. When the alignment interface is inserted into the reservoir holder, the first alignment feature may cooperate with the corresponding alignment feature of the reservoir holder so as to rotate the alignment interface and thereby align the alignment interface within the reservoir holder. By aligning the alignment interface, the reservoir may also be aligned to the reservoir holder, when the reservoir is coupled to the main body of the alignment interface.

According to an embodiment, the alignment feature is provided on a sidewall of said main body. Additionally or alternatively, the alignment feature may be provided on a distal end face of said main body. Additionally or alternatively, the alignment feature may be provided on a flange of said main body.

According to an embodiment, said corresponding alignment feature comprises a ramp provided on said holder. The ramp may be provided along an inner surface of the reservoir holder. Additionally or alternatively, said corresponding alignment feature may comprise at least one protrusion. The corresponding alignment feature may comprise a plurality of protrusions. Additionally or alternatively, said corresponding alignment feature may comprise at least one groove. The corresponding alignment feature may comprise a plurality of grooves.

According to an embodiment, said main body comprises a bore. Said bore may define a diameter configured to receive said reservoir. Said main body may be permanently or releasably mounted on said reservoir. Said reservoir may have a neck part. The neck part may be pressed into said bore of said alignment interface.

According to an embodiment, said alignment interface comprises a thread. The thread may be configured for receiving a threaded needle hub.

According to an embodiment said alignment feature prevents relative rotation between said reservoir holder and said alignment interface. The alignment feature may thus prevent relative rotation between said reservoir holder and said reservoir when the reservoir was positioned into the holder.

According to an embodiment, the alignment interface comprises a coding feature. The alignment interface may comprise a plurality of coding features. The coding feature may be a mechanical coding feature. The first alignment feature may comprise said coding feature.

According to an embodiment, said alignment feature or coding feature comprises a first protrusion. The first protrusion may be provided on said main body of said alignment interface. Said first alignment feature or coding feature may comprise a second protrusion. The second protrusion may be provided on said main body of said alignment interface. A radius of said second protrusion may be greater than a radius of said first protrusion.

According to an embodiment, a geometry, e.g. an outer shape, of said alignment interface is designed to carry information about the contents of the cartridge or reservoir. In particular, the alignment feature may provide information about a medicament held in the reservoir.

In yet another alternative arrangement, a drug delivery system may be provided. The drug delivery system may comprise a drug delivery device, e.g. a pen-type device such as a pen-type injector. The device may be a reusable device. Alternatively, the device may be a disposable device. The device may comprise a dose setting mechanism. The drug delivery system may comprise a reservoir holder or cartridge holder configured to hold a reservoir or cartridge. The cartridge holder may be permanently or removably secured to the dose setting mechanism. A reservoir or cartridge may be permanently or removably contained within the cartridge holder. The drug delivery system may comprise an alignment interface. The alignment interface may be configured to, preferably rotatably, align the cartridge within the cartridge holder. According to an embodiment, said alignment interface comprises a main body. The main body may be permanently or releasably coupled to said cartridge. Said first alignment feature may be provided on said main body. The alignment interface may comprise a first alignment feature. The first alignment feature may cooperate with a corresponding alignment feature, e.g. a groove, provided by the cartridge holder so as to align the alignment interface in the holder, thus aligning the cartridge in the holder when a cartridge is coupled to the main body of the alignment interface. The alignment interface may also prevent rotation of the cartridge within the cartridge holder.

According to an embodiment, the dose setting mechanism comprises a piston rod such as a rotating piston rod. The piston rod may be configured for expelling a set dose from the cartridge.

According to a preferred embodiment, an alignment interface for aligning a reservoir within a reservoir holder is provided, said interface comprising a main body coupled to said reservoir and a first alignment feature provided on said main body. When said reservoir is inserted into said reservoir holder, said first alignment feature cooperates with a corresponding alignment feature of said reservoir holder so as to rotate said reservoir and thereby align said reservoir within said holder.

According to a preferred embodiment, a system for a drug delivery device is provided which comprises a reservoir holder and a reservoir. The reservoir holder is configured to hold the reservoir. The system comprises an alignment interface for aligning the reservoir within the reservoir holder. The alignment interface comprises a main body coupled to the reservoir and a first alignment feature provided on the main body. When the reservoir is inserted into the reservoir holder, the first alignment feature cooperates with a corresponding alignment feature of the reservoir holder so as to rotate the reservoir and thereby align the reservoir within the reservoir holder.

According to a preferred embodiment, a drug delivery system is provided comprising a drug delivery device comprising a dose setting mechanism and the previously described system for a drug delivery device. The reservoir holder is secured to the dose setting mechanism the reservoir is contained within the reservoir holder.

According to a preferred embodiment, a drug delivery system is provided, said system comprising a drug delivery device comprising a dose setting mechanism, a cartridge holder secured to said dose setting mechanism and a cartridge contained within said cartridge holder. The drug delivery system further comprises an alignment interface for rotatably aligning said cartridge within said cartridge holder.

These as well as other advantages of various aspects of the present invention will become apparent to those of ordinary skill in the art by reading the following detailed description, with appropriate reference to the accompanying figures.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE FIGURES

Exemplary embodiments are described herein with reference to the figures, in which.

DETAILED DESCRIPTION

Figure 1:
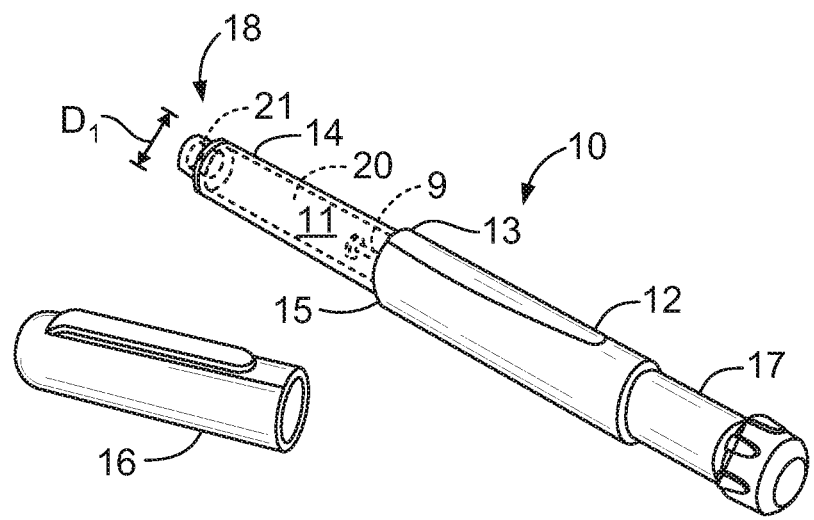
FIG. 1 illustrates an exemplary pen-type drug delivery device.

Referring to FIG. 1, there is shown a drug delivery device 10 in the form of a pen-type syringe. This drug delivery device 10 comprises a dose setting mechanism 12, a cartridge holder 14, and a removable cap 16. A proximal end 15 of the cartridge holder 14 and a distal end 13 of the dose setting mechanism 12 are removably secured together. The pen-type syringe may comprise a re-usable or a disposable pen-type syringe. Where the syringe comprises a re-usable device, the cartridge holder 14 and the dose setting mechanism 12 are removably coupled together. In a disposable device, they are permanently coupled together. In FIG. 1, the dose setting mechanism 12 comprises a piston rod 9, such as a threaded piston rod that rotates when a dose is injected.

To inject a previously set dose, a double ended needle assembly is attached to a distal end 18 of the cartridge holder 14. Preferably, the distal end 18 of the holder 14 comprises a thread 21 (or other suitable connecting mechanism such as a snap lock, snap fit, form fit, or bayonet lock mechanism) so that the needle assembly may be removably attached to the distal end 18 of the holder 14. When the drug delivery device 10 is not in use, the removable cap 16 can be releasably retained over the cartridge holder 14.

Figure 2:
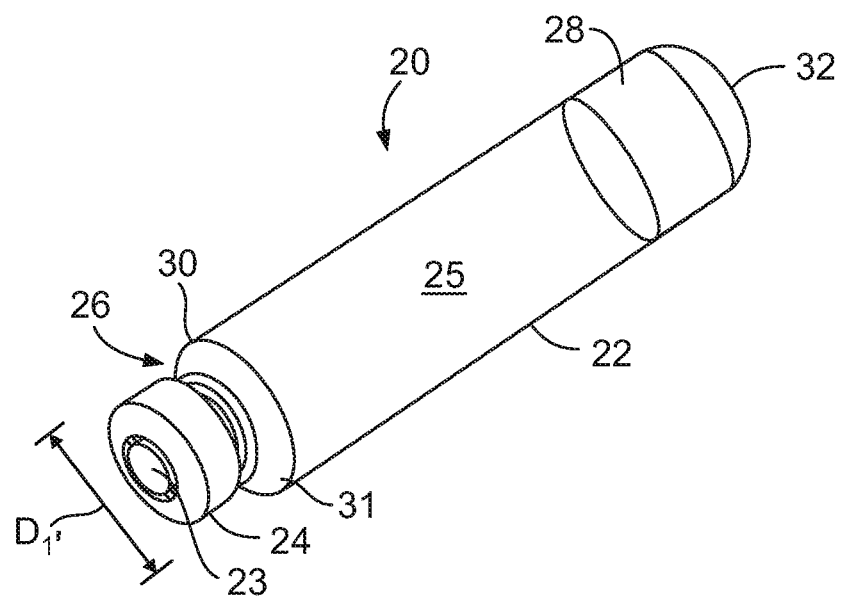
FIG. 2 illustrates a cartridge that may be loaded into a cartridge holder of the pen-type drug delivery device illustrated in FIG. 1.

An inner cartridge cavity 11 defined by the cartridge holder 14 is dimensioned and configured to securely receive and retain a cartridge 20. FIG. 2 illustrates a perspective view of the cartridge 20 that may be used with the drug delivery device 10 illustrated in FIG. 1. The cartridge 20 includes a generally tubular barrel 22 extending from a distal end 30 to a proximal end 32. The distal end 30 is defined by an inwardly converging shoulder 31.

At the distal end 30, the cartridge 20 includes a smaller diameter neck 26 and this neck 26 projects distally from the shoulder 31 of the barrel 22. Preferably, this smaller diameter neck 26 is provided with a large diameter annular bead (not shown) and this bead extends circumferentially thereabout at the extreme distal end of the neck 26. A pierceable seal or septum 23 is securely mounted across the open distal end defined by the neck 26. The seal 23 may be held in place by a metallic sleeve or ferrule 24. This ferrule 24 may be crimped around the circumferential bead at the distal end of the neck 26. A medicament 25 is pre-filled into the cartridge 20 and is retained within the cartridge 20, in part, by the pierceable seal 23, the metallic sleeve or ferrule 24, and a stopper 28. The stopper 28 is in sliding fluid-tight engagement with the inner tubular wall of the barrel 22. Axially directed forces acting upon the stopper 28 during dose injection or dose administration urges the medicament or medication 25 from the cartridge 20 though a double ended needle mounted onto the distal end 30 of the cartridge holder 14 and into the injection site. Such axially forces may be provided by the piston rod 9.

A portion of the cartridge holder 14 defining the cartridge holder cavity 11 is of substantially uniform diameter represented in FIG. 1 by $D_1$. This diameter $D_1$ is preferably slightly greater than the diameter $D_{1'}$ of the cartridge 20. The interior of the cartridge holder 14 includes an inwardly-extending annual portion or stop that is dimensioned to prevent the cartridge 20 from moving within the cartridge holder 14. In this manner, when the cartridge 20 is loaded into the cavity 11 of the cartridge holder 14 and the cartridge holder 14 is then connected to the dose setting member 12, the cartridge 20 will be securely held within the cartridge cavity 11. More particularly, the neck 26 and ferrule 24 of the cartridge 20 are inserted in a proximal to distal direction into the open proximal end of the cartridge holder 14 with the ferrule 24 eventually passing entirely into the holder 14. With the holder 14 removably coupled to the dose setting mechanism 12, the proximal end of the cartridge 20 will typically abut a stop provided by the dose setting member 12.

A number of doses of the medicament 25 may be dispensed from the cartridge 20. Preferably, the cartridge 20 contains a type of medicament 25 that must be administered often, such as one or more times a day. One such medicament is insulin. The movable piston or stopper 28 is retained in a first end or proximal end of the cartridge 20 and receives an axial force created by the piston rod 9 of the dose setting mechanism 12.

The dose setting mechanism 12 comprises a dose setter 17 at the proximal end of the dose setting mechanism. In one preferred arrangement, the dose setter 17 is rotated to set a dose. To administer this set dose, the user attaches the needle assembly comprising a double ended needle on the distal end 18 of the cartridge holder 14. In this manner, the needle assembly pierces the seal 23 of the cartridge 20 and is, therefore, in liquid communication with the medicament 25. The user pushes on the dose setter 17 to inject the set dose. The same dose setting and dose administration procedure is followed until the medicament 25 in the cartridge 20 is expended and then a new cartridge must be loaded in the device 10. To exchange an empty cartridge, the user is called upon to remove the cartridge holder 14 from the dose setting mechanism 12.

Figure 3:
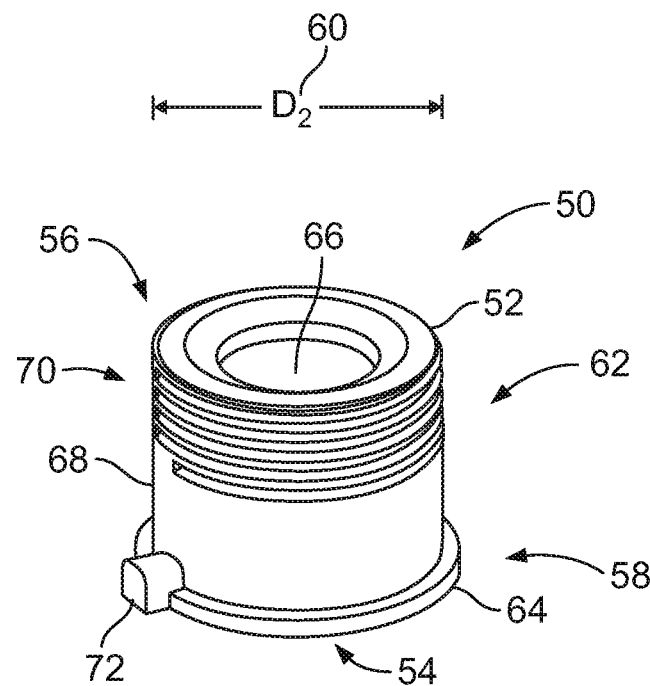
FIG. 3 illustrates a first arrangement of an alignment interface for use with a cartridge that may be used with a pen-type drug delivery device, such as the drug delivery device illustrated in FIG. 1.

FIG. 3 illustrates a first arrangement of an alignment interface 50 for use with a cartridge that may be used with a pen-type drug delivery device, such as the cartridge 20 illustrated in FIG. 2. More specifically, the alignment interface 50 is snapped over the distal end of the cartridge 20 such that the interface 50 form fits or snaps around the ferrule 24 of the cartridge 20. In this manner, and as explained in greater detail below, the interface 50 can provide an alignment feature, a non-rotational feature, and/or a mechanical coding feature to the cartridge 20.

The alignment interface 50 shown in FIG. 3 comprises a cylindrically shaped main body 52 defining a centrally located aperture or bore 54. This aperture 54 extends from a proximal end 58 to a distal end 56 of the main body 52 and, when in use, the aperture 54 is placed over the ferrule 24 located at the distal end of the cartridge 20. Preferably, this main body 52 has a diameter $D_2$ 60 that is slightly larger than the diameter of the ferrule 24 of the cartridge 20. The alignment interface 50 further comprises an axially extending wall or sidewall 62 that extends from a flange 64 located near the proximal end of the main body 52. This axially extending wall 62 extends towards the distal end 56 of the main body 52.

Near the distal end 56, the alignment interface 50 is provided with a pass through 66. In one arrangement, this pass through 66 is sized or configured so that, when the alignment interface 50 is snapped over the ferrule 24 of the cartridge 20, the pass through 66 will expose a portion of the ferrule 24 of the cartridge 20 and will provide access to at least a portion of the pierceable seal 23 of the cartridge 20.

In one arrangement, the alignment interface 50 is intended for use with a standard double ended needle wherein this needle comprises a hub having an internal thread. As such, an outer surface 68 of the vertical wall or sidewall 62 of the main body 52 is provided with an outer thread 70 that receives such a hub of the double ended needle. Such an outer thread 70 could comprise a single or a double start outer thread. In addition, when such double ended needle is mounted onto the alignment interface 50, the piercing distal needle projects through the pass through 66 and into the pierceable seal 23 of the cartridge 20.

In this preferred arrangement, the flange 64 is provided with at least one alignment feature 72. In this illustrated arrangement, the alignment feature 72 comprises a generally rounded rectangular shape and extends out past the diameter $D_2$ 60 of the main body 52. However, those of skill in the art will recognize, alternative geometries of this alignment feature 72 may also be used. In addition, in this preferred arrangement, the alignment feature 72 comprises a single protrusion that is directed radially outwards away from the main body 52. In this preferred arrangement, when mounted onto a cartridge 20, the protrusion 72 extends beyond an outside diameter of a cartridge 20, such as diameter $D_{1'}$ of cartridge 20 (FIG. 2).

Figure 4:
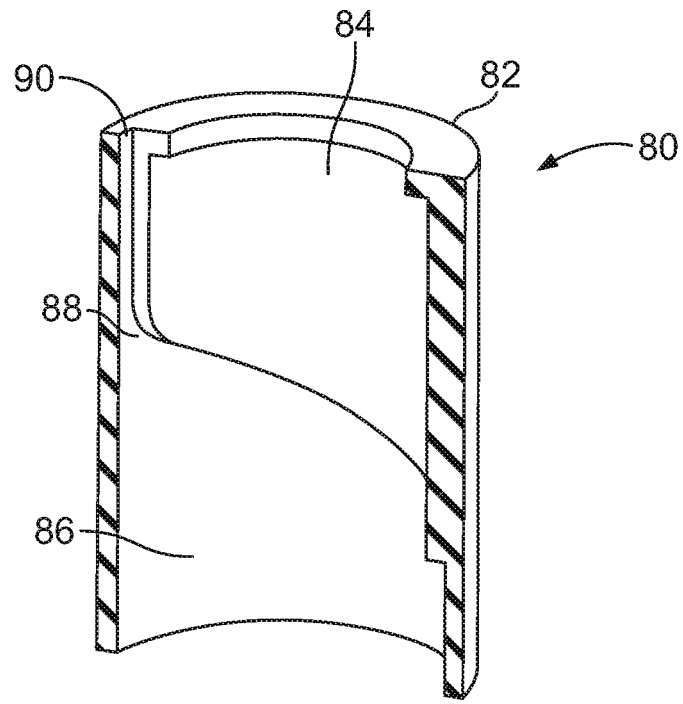
FIG. 4 illustrates a distal cartridge holder portion that may be used with the alignment interface illustrated in FIG. 3.

The alignment interface 50 is intended for use with a cartridge holder similar to the cartridge holder 14 of FIG. 1 but somewhat modified. For example, FIG. 4 illustrates a cross-sectional view of a distal end 82 of a modified reservoir holder or cartridge holder 80 that could be used with the alignment interface 50 having a single protrusion feature 72. The proximal end (not shown) of the cartridge holder 80 would include a similar releasable connection mechanism (e.g., thread, snap lock, snap fit, bayonet lock, etc.) as the cartridge holder 14 illustrated in FIG. 1.

Figure 5:
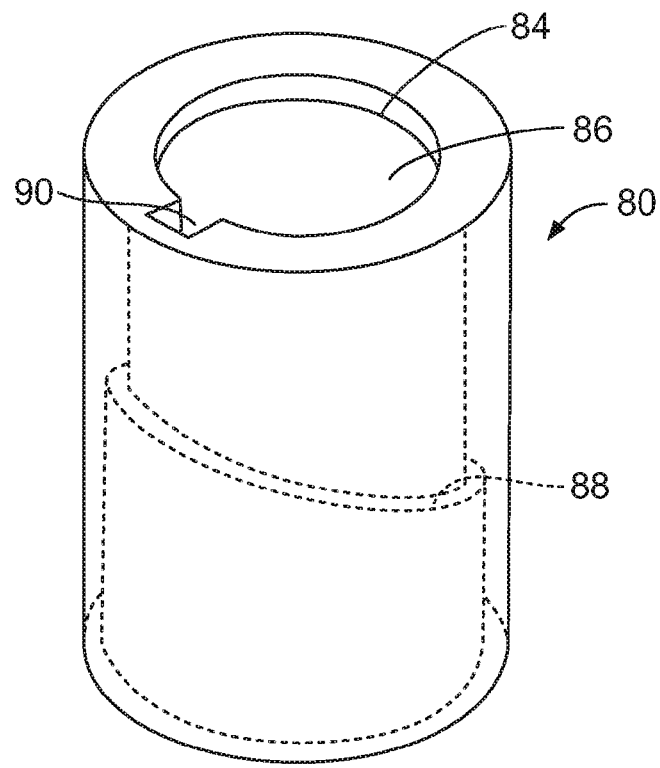
FIG. 5 illustrates a three-dimensional perspective view of the distal cartridge holder portion illustrated in FIG. 4.

In this modified cartridge holder 80, the threaded distal end 18 of the cartridge holder 14 illustrated in FIG. 1 is removed since this thread (or similar connection mechanism) is now provided by the alignment interface 50. FIG. 5 illustrates a three-dimensional perspective view of the distal cartridge holder portion illustrated in FIG. 4. As can be seen from FIGS. 4 and 5, the cartridge holder 80 now comprises a bore or aperture 84 located near the distal end 82 of the holder 80.

In addition, and as can be seen when comparing the cartridge holder 14 of FIG. 1 with the cartridge holder 80 in FIG. 4, an inner wall 86 of the modified cartridge holder 80 defines a ramp 88 having a predefined ramp projection around an inner circumference. This ramp 88 is so configured that, when a cartridge with a correctly coded alignment interface is inserted into a proximal end of the cartridge holder 80, the ramp 88 guides the radially extending protrusion 72 of the alignment interface 50 to an end alignment position 90 located at the distal end 82 of the holder 80. In this manner, the correct combination of the radially extending protrusion 72 and ramp projection will allow the distal end of the alignment interface 50 to pass through the bore 84. Consequently, when a cartridge 20 carrying the alignment interface 50 is inserted into the cartridge holder 80, the alignment feature 72 cooperates with the ramp 88 until the alignment interface resides in a final alignment position 90.

Figure 6:
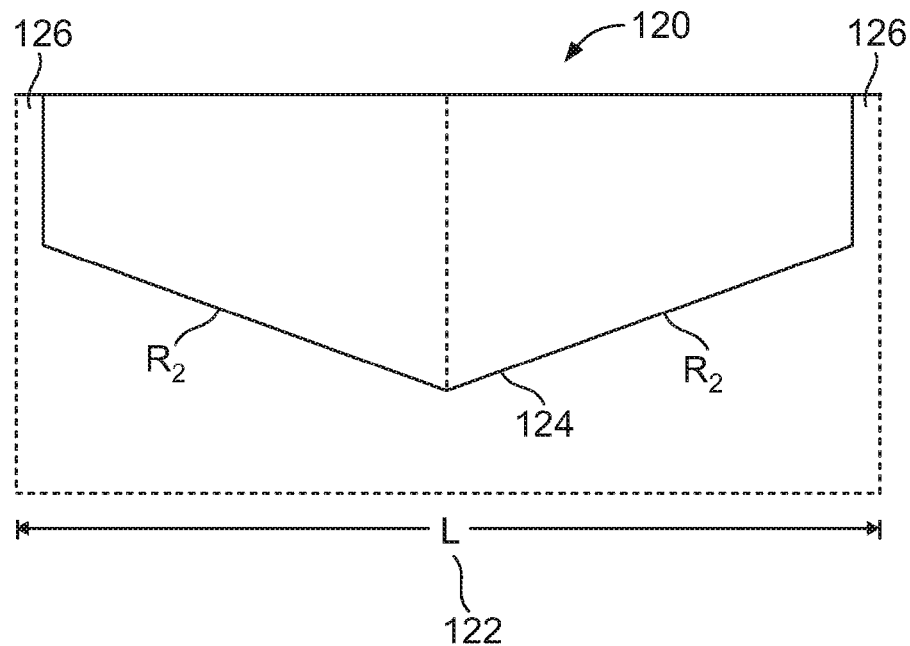
FIG. 6 illustrates a ramp projection around the circumference of the distal cartridge holder portion illustrated in FIGS. 4 and 5.

FIG. 6 illustrates a schematic representation of the ramp projection 120 provided on the inner wall of the cartridge holder 80 illustrated in FIG. 4. In this illustration, the length L 122 of the ramp projection 88 will be generally larger than the outer circumference of the cartridge 20. This ramp projection 120 around the circumference comprises a single ramp 124 ending in a final alignment position 126.

When a cartridge containing the alignment interface 50 is placed within the cartridge holder 80 and the alignment feature 72 travels both axially and rotationally into the cartridge holder 80 (either pushed manually or under gravity), the contact between the protrusion 72 and the ramp 88 causes the cartridge to rotate. That is, when the cartridge is placed into the proximal end of the cartridge holder 80, the alignment feature 72 will travel along either R1 or R2 of the ramp projection around the circumference 120. This feature 72 will eventually align the cartridge within the cartridge holder 80 with the feature 72 eventually residing in the final alignment position 126. By adjusting the angles of the ramped projection around the circumference R1, R2, the insertion force required to align the alignment interface 50 (and, hence, the cartridge) within the cartridge holder 80 can be increased or decreased. In this manner, the alignment feature 50 may help a user align coding on the cartridge with corresponding coding on the cartridge holder 80. The coding might comprise additional features aside from the protrusion 72 or alternatively, the protrusion 72 could be provided with some type of coding feature such as a particular size or dimension of the protrusion. In yet another arrangement, this coding could be provided by the number of protrusions provided on the main body 52 or perhaps the location of the protrusion on the main body 52.

Figure 7:
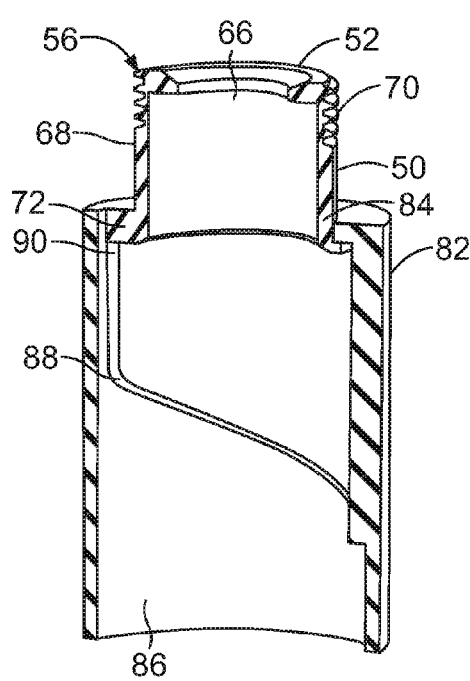
FIG. 7 illustrates the alignment interface illustrated in FIG. 3 attached to the distal cartridge holder portion illustrated in FIG. 5 (without a cartridge)

One advantage of using the alignment interface 50 is that the cooperation between the alignment feature 72 and corresponding ramp 88 prevents the alignment interface 50 (and, hence, the cartridge) from unwanted rotation within the cartridge holder 80. That is, the alignment feature 72 prevents unwanted rotation of the alignment interface 50 when a double ended needle is either attached or removed from the distal end of the alignment interface 50. FIG. 7 illustrates the alignment feature 72 in the end alignment position 90 (the cartridge has been omitted for clarity) where the distal end 56 of the alignment interface 50 is allowed to pass through the cartridge holder bore 84.

Figure 8:
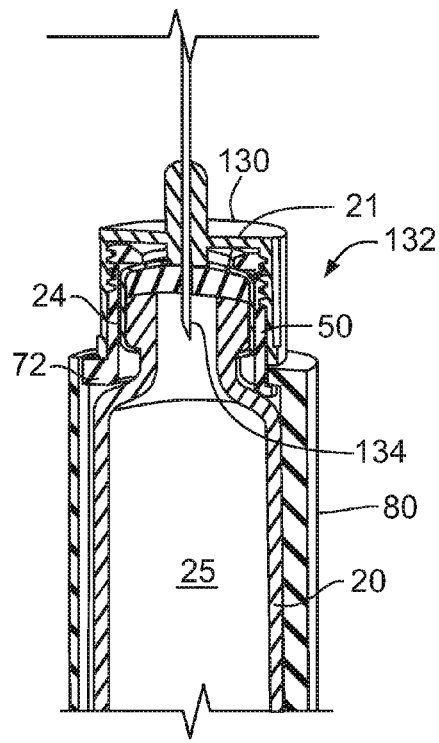
FIG. 8 illustrates the alignment interface illustrated in FIG. 3 attached to the distal cartridge holder portion illustrated in FIG. 5 with a cartridge and a double ended needle.

FIG. 8 illustrates schematically the relevant parts of the drug delivery device 10 with a needle assembly mounted onto the interface arrangement 50 illustrated in FIG. 3. As illustrated, cartridge 20 has a neck with a flange against which a rubber membrane or seal 23 is secured by a ferrule 24 beaded under the flange. The bottom of the cup shaped cap or neck has an opening up through which part of the membrane 23 protrudes. The interface 50 is passed with its bore over the cap and pressed down to make the protrusion pass the ferrule 24 and grip under the lower beaded edge of this cap. A needle assembly 130 has a depending tubular skirt 132 having an internal thread to be screwed onto the outer thread of the interface 50 with its needle 134 piercing the membrane 23 and projecting into the opening of the neck part of the cartridge 20. This is just one arrangement of how the disclosed alignment interface 50 may be used to align the cartridge 20 within the cartridge holder 80.

In this manner, when a user attempts to load the cartridge 20 into the cartridge holder 80, the alignment interface 50 and ramp 88 will cooperate so as to allow insertion of an acceptable cartridge. Alternatively, if an incorrect alignment interface is used, the alignment interface and ramp 88 will not cooperate and will, therefore, prohibit an incorrect cartridge from being inserted into a drug delivery device. Depending on the mechanical structure of the drug delivery device 10, the alignment interface 50, or the drug administration system, the coding projection (or plurality of projections or projection arrays) may be provided along a different portion of the cartridge 20. For example, the coding projection could be provided along the tubular member 22 of the cartridge 20 or, alternatively, towards the proximal end of the cartridge 20.

Although the alignment feature 72 on the interface 50 is shown as a single protrusion, the alignment feature 72 could comprise an indentation that matches a corresponding protrusion located on the internal wall of the cartridge holder 80.

Figure 9:
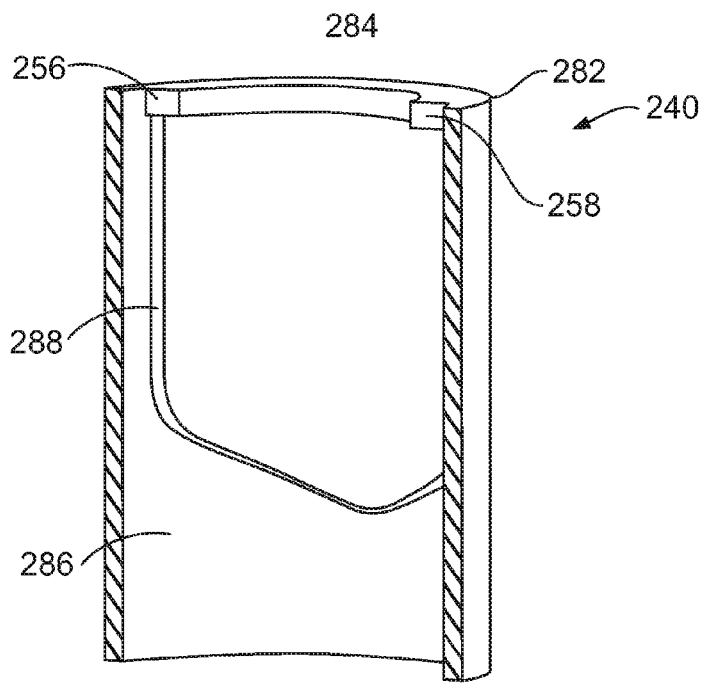
FIG. 9 illustrates a second arrangement of a distal cartridge holder portion that may be used with an alignment interface.

More than one protrusion or indentation around the circumference may also be provided. One advantage of having two alignment features 72 is that the ramp 88 can have a shorter axial extent for the same ramp angle, and the cartridge 80 does not have to rotate as much to align the coding. For example, FIG. 9 illustrates a second arrangement of a distal cartridge holder portion 240 that may be used with an alternative alignment interface. In this arrangement, the distal cartridge holder 240 is configured for an alignment interface having two radially protruding features, which, in one arrangement, are preferably geometrically similar and evenly spaced around the circumference. Similar to the distal cartridge holder 80 illustrated in FIG. 4, this holder 240 comprises distal end 282, a bore 284, an inner wall 286, and a ramp 288.

Figure 10:
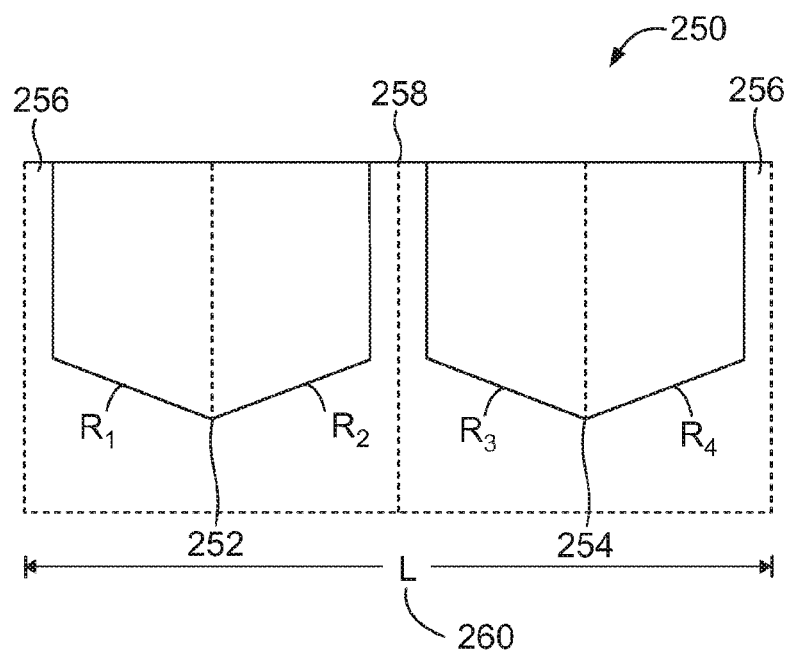
FIG. 10 illustrates a ramp projection around the circumference of the distal cartridge portion illustrated in FIG. 9.

FIG. 10 illustrates the ramp projection 250 of the distal cartridge portion 240 illustrated in FIG. 9. This projection 250 is provided on the inner wall 286 of the cartridge holder 240 illustrated in FIG. 9. In this illustration, the length L 260 of the ramp profile is equal to the circumference of the cartridge holder 240. This ramp profile 250 comprises two ramps 252, 254 that terminate in final alignment positions 256, 258. By adjusting the angles of the ramped profile R1, R2, R3, and R4, the insertion force required to align the alignment interface (and, hence, the cartridge) with the cartridge holder 240 may be increased or decreased.

When a cartridge containing an alignment interface having two protrusions is placed within the cartridge holder 240, the two alignment features travel axially and rotationally into the cartridge holder 240 (either pushed manually or under gravity), the contact between the protrusions and the ramps 252, 254 causes the cartridge to rotate. That is, the alignment features will travel along either R1 and R3 or R2 and R4 of the ramp profile and then, eventually, align the cartridge within the cartridge holder 240 with the features residing in the final alignment positions 256, 258.

Figure 11:
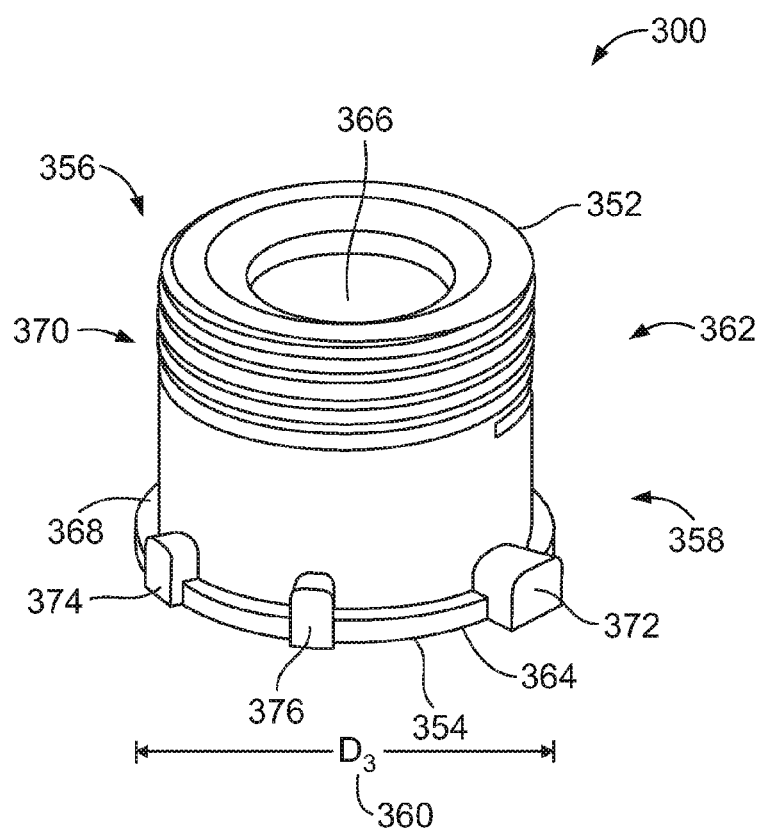
FIG. 11 illustrates an alternative arrangement of an alignment interface for use with a cartridge that may be used with a pen-type drug delivery device, such as the drug delivery device illustrated in FIG. 1.

FIG. 11 illustrates an alternative arrangement of an alignment interface 300 for use with a cartridge, such as the cartridge 20 illustrated in FIG. 2. More specifically, the alignment interface 300 is snapped over the distal end 18 of the cartridge 20 such that it fits around the ferrule 24 of the cartridge 20 and thereby provides a mechanical coding to the cartridge 20.

The alignment interface 300 shown in FIG. 11 comprises a cylindrically shaped main body 352 defining a centrally located aperture 354. This aperture extends from a proximal end 358 to a distal end 356 of the main body 352. Preferably, this main body has a diameter $D_3$ 360 that is slightly larger than the diameter of the ferrule 24 of the cartridge 20. The alignment interface 300 further comprises an axially extending wall 362 that extends from a flange 364 located near the proximal end of the main body 352. This axially extending wall 362 extends towards the distal end 356 of the main body 352.

Near the distal end 356, the alignment interface 300 is provided with a pass through 366. This pass through 366 is sized or configured so that, when the alignment interface 300 is snapped over the ferrule 24 of the cartridge 20, the pass through 366 exposes a portion of the ferrule 24 of the cartridge 20 and provides access to at least a portion of the pierceable seal 23 of the cartridge 20. The alignment interface 300 is intended for use with a standard double ended needle comprising a hub having an internal thread. As such, an outer surface 368 of the vertical wall 362 is provided with an outer thread 370 that receives a hub of the double ended needle. Such an outer thread 370 could comprise a single or a double start outer thread. In addition, when such double ended needle is mounted onto the alignment interface 300, the piercing distal needle will project through the bore and into the pierceable seal 23 of the cartridge 20.

In this preferred arrangement, the flange 364 is provided with at least one alignment feature 372. In addition to the alignment feature 372, interface 300 further comprises a first and a second coding feature 374, 376. These coding features 374, 376 allow the interface 300 to be mechanically coded to the inner wall of the cartridge holder.

Figure 12:
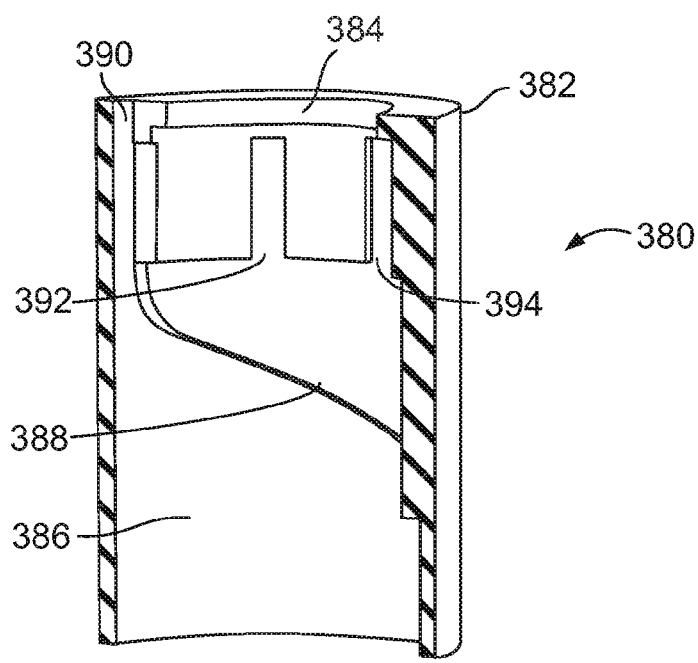
FIG. 12 illustrates a distal cartridge holder portion that may be used with the alignment interface illustrated in FIG. 11.

For example, FIG. 12 illustrates a cross-sectional view of a distal end 382 of a modified cartridge holder 380 that could be used with the alignment interface 300 illustrated in FIG. 11. This cartridge holder 380 comprises a bore 384 located near the distal end 382 of the holder. In addition, an inner wall 386 of the cartridge holder 380 defines a ramp 388 having a profile for use with an interface having a single protrusion and a first and second coding feature. This ramp 388 is so configured that, when cartridge 20 with a correctly coded alignment interface is inserted into a proximal end of the cartridge holder, the ramp guides the radially extending protrusion or alignment feature 372 of the alignment interface 300 to an end alignment position 390 located at the distal end 382 of the holder 380. In this manner, when a cartridge 20 carrying the alignment interface 300 is inserted into the cartridge holder 380, the alignment feature 372 cooperates with the ramp 388 until the alignment interface 300 resides in a final alignment position 390. Ramp 388 is also configured to guide the first and second coding features 374, 376 into a first and a second coding receiving areas 392, 394.

Figure 13:
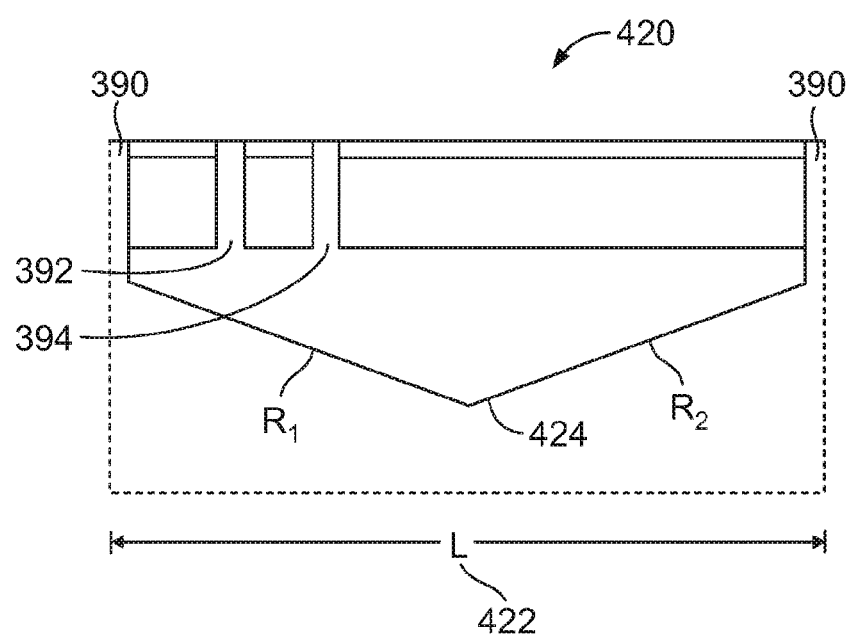
FIG. 13 illustrates a ramp projection around the circumference of the distal cartridge portion illustrated in FIG. 12.

FIG. 13 illustrates a ramp profile 420 of the ramp 388 provided on the inner wall of the cartridge holder 380 illustrated in FIG. 12. In this illustration, the length L 422 of the ramp profile 420 is equal to the circumference of the cartridge 20. This ramp profile 420 comprises a single ramp 424 ending in a final alignment position 390.

Figure 14:
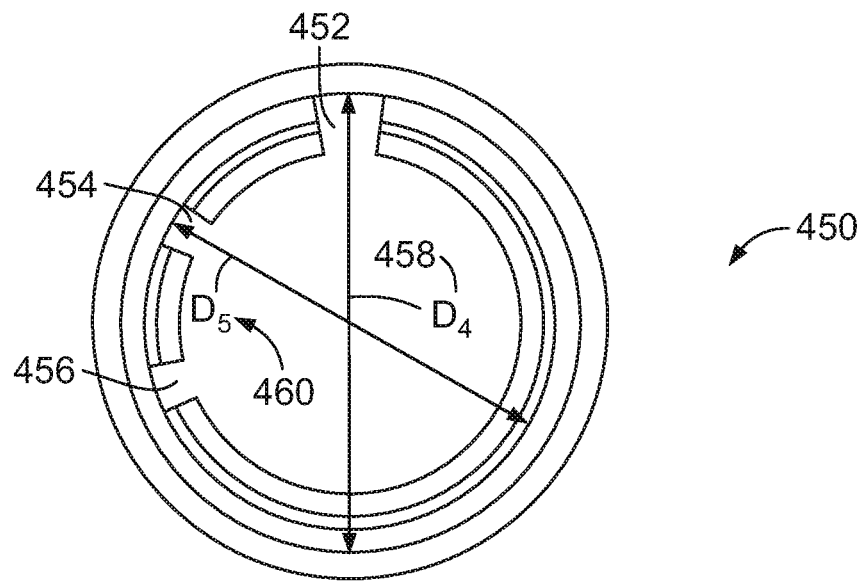
FIG. 14 illustrates a top perspective view of the distal cartridge portion illustrated in FIG. 11.

FIG. 14 illustrates a top perspective view 450 of the distal cartridge holder portion illustrated in FIG. 12. As can be seen from FIG. 14, the distal end 382 of the cartridge holder 380 comprises an alignment notch 452 and coding notches 454, 456. The alignment notch 452 has a diameter $D_4$ 458 which is greater than the diameter of the coding slot $D_5$ 460. The diameter $D_4$ of the alignment notch 452 is larger than that of the coding notches $D_5$ so as to prevent the alignment feature 372 from catching on the coding notches 454, 456. Although only one protrusion and only two coding features are illustrated in this alignment arrangement 300, it will be understood that alternative combinations and arrangement of protrusions and codings could be used.

This change in surface height near the distal end of the holder 380 can provide a coding feature that fits within a corresponding raised area on the inner wall of the cartridge holder 380. Matching the interface 300 and inner wall of the cartridge holder 380 together on insertion of the cartridge 20 into the cartridge holder 380 will confirm to the user that a correct cartridge has been loaded into the cartridge holder 380 and, hence, the drug delivery device 10.

Although the alignment interface 300 is illustrated as being coupled around the ferrule 24 to the distal end of a cartridge 20, alternative alignment interface arrangements may also be used. For example, the alignment feature and/or coding may be added to an alignment interface this is provided at another location, such as a ring around a sidewall of the cartridge 20. The coding may be mechanical features that mate with each other, or it may be read electronically. Alternatively, the alignment interface may take the form of ridges or grooves provided along the cartridge glass or moulding. In addition, the ferrule 24 itself of the cartridge 20 may be provided with an alignment interface that cooperates with an inner surface of the cartridge holder.

Figure 15:
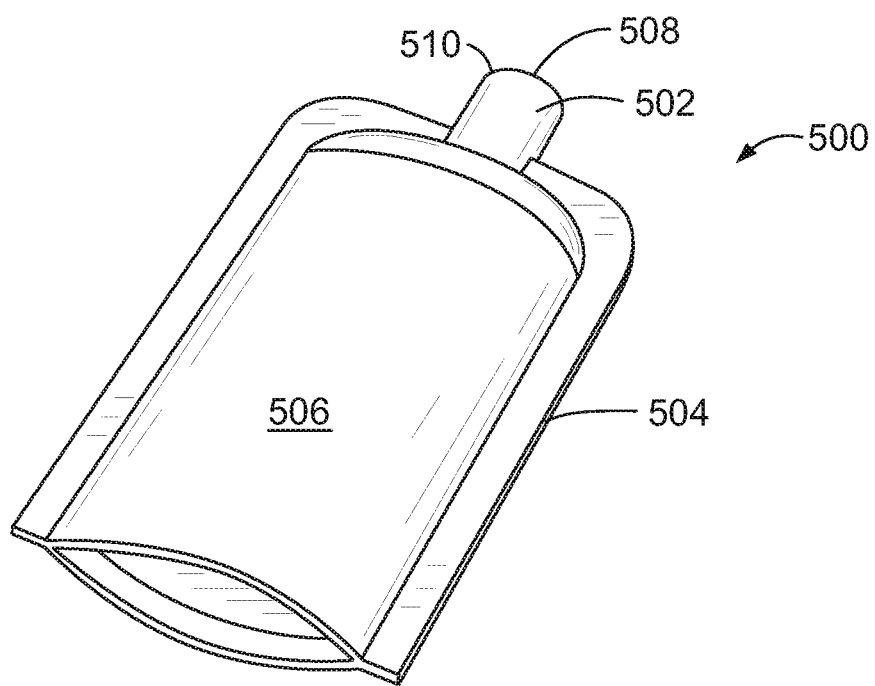
FIG. 15 illustrates an alternative reservoir that may be used with another alignment interface.

In other situations, the disclosed coding system may apply to any drug delivery device, with any type of reservoir or primary pack, e.g. inhaler, pouch. For example, FIG. 15 illustrates a drug reservoir 500 comprising a vessel 504 that contains a medicament 506. A stopper 508 is provided along a distal end of the vessel 504 and is attached to the vessel 504 so as to prevent the medicament 506 from exiting the vessel 504. An alignment feature 502 is provided on the vessel 504. In this preferred arrangement, the alignment feature 502 is provided near an output port 510 of the vessel 504 but may also be provided at alternative locations. This output port 510 has a rigid neck and the alignment feature 502 is provided along this neck so as to interface with a reservoir holder.

The disclosed alignment system results in a number of advantages. For example, the disclosed alignment system may assist a user to distinguish between medicaments, thereby helping to ensure that a delivery device can only be used with a medicament for which the device is intended. Therefore, with the disclosed alignment interface system applied to a cartridge, the cartridge is prevented from being loaded into any other drug delivery device by loading a cartridge with an incorrect or unwanted interface. The disclosed cartridge alignment interface may prevent a user from completing one or more of the following actions: fully inserting the cartridge into an incorrect cartridge holder or attaching the cartridge and/or cartridge holder onto an incorrect dose setting mechanism. With certain existing coding systems, the user is called upon to manually align coding on one part with corresponding features on the other part. Users with limited dexterity might find this difficult, so the coding features must be large, and, therefore, combinations are limited. With the disclosed system, complex codes can be aligned automatically, no matter in what orientation the user inserts the cartridge into the holder.

The disclosed alignment interface may also result in a low cost coding mechanism since the interface does not require a large number of parts and can be manufactured in a cost effective manner. Moreover, there are quite a large number of different coding configurations between the interface and the cartridge holder that may be used. Consequently, with the disclosed alignment interface schemes, a large number of medicaments can be distinguished from one another. In addition, with the disclosed alignment interface schemes, if a user attempts to load an incorrect reservoir into a cartridge holder designed for a different cartridge, the user will be alerted at an early stage of the assembly process.

We claim:

1. A system for a drug delivery device comprising:
a reservoir holder configured to hold a reservoir, where the reservoir holder comprises a bore having an inner wall comprising a ramp profile which comprises a single ramp terminating in an end alignment position, wherein the length of the ramp profile is equal to the circumference of the reservoir holder;
an alignment interface comprising a main body configured to be coupled to the reservoir and a first alignment feature provided on the main body configured to engage the ramp as the reservoir is inserted into the bore of the reservoir holder; and
one or more coding features,
wherein, when the alignment interface is inserted into the reservoir holder, the engagement of the first alignment feature with the ramp of the reservoir holder causes the alignment interface to rotate and thereby align and engage the first alignment feature with the end alignment position.

2. The system of claim 1, wherein the first alignment feature comprises at least one protrusion or at least one groove provided on the main body of the alignment interface.

3. The system according to claim 1, wherein the main body comprises a bore, the bore defining a diameter configured to receive the reservoir.

4. The system according to claim 1, further comprising the reservoir, wherein the main body is mounted on the reservoir, and wherein the reservoir comprises a neck part that is pressed into an aperture of the alignment interface.

5. The system according to claim 1, wherein the alignment interface comprises a thread configured for receiving a threaded needle hub.

6. The system according to claim 1, wherein the alignment feature is configured to prevent relative rotation between the reservoir holder and the alignment interface when the reservoir is within the reservoir holder.

7. The system according to claim 1, wherein the first alignment feature comprises a coding feature.

8. The system according to claim 1, wherein the first alignment feature comprises a first protrusion provided on the main body of the alignment interface.

9. The system according to claim 8, wherein the first alignment feature comprises a second protrusion provided on the main body, and wherein a radius of the second protrusion is greater than a radius of the first protrusion.

10. The system according to claim 1, wherein the first alignment feature is provided on a sidewall of the main body, on a distal end face of the main body, and/or on a flange of the main body.

11. The system according to claim 1, wherein a geometry of the alignment interface is designed to carry information about the contents of the reservoir.

12. A drug delivery system comprising:
a drug delivery device comprising a dose setting mechanism and the system according to claim 1,
wherein the reservoir holder is secured to the dose setting mechanism and wherein the reservoir is contained within the reservoir holder.

13. The drug delivery system according to claim 12, wherein the first alignment feature of the alignment interface mechanically cooperates with the corresponding alignment feature provided by the reservoir holder so as to align the reservoir in the reservoir holder.

14. The drug delivery system of claim 12, wherein the reservoir holder is removably secured to the dose setting mechanism and wherein the reservoir is removably contained within the reservoir holder.

15. The drug delivery system according to claim 12, wherein the drug delivery device comprises a reusable drug delivery device.

16. The drug delivery system according to claim 12, wherein the dose setting mechanism comprises a rotating piston rod for expelling a set dose from the reservoir.

17. A system for a drug delivery device comprising:
a reservoir holder configured to hold a reservoir, where the reservoir holder comprises a bore having an inner wall comprising a ramp profile which comprises exactly two ramps terminating in end alignment positions wherein the length of the ramp profile is equal to the circumference of the reservoir holder,
an alignment interface comprising a main body configured to be coupled to the reservoir and a first alignment feature provided on the main body configured to engage the ramp or protrusion as the reservoir is inserted into the bore of the reservoir holder; and
one or more coding features, wherein, when the alignment interface is inserted into the reservoir holder, the engagement of the first alignment feature with the ramp of the reservoir holder causes the alignment interface to rotate and thereby align and engage the first alignment feature with the end alignment position.

* * * * *